(12) United States Patent
Jamshidi

(10) Patent No.: US 8,236,030 B2
(45) Date of Patent: Aug. 7, 2012

(54) ADVANCED INTRA-SPINAL DECOMPRESSION IMPLANT

(75) Inventor: Saied Jamshidi, Potomac, MD (US)

(73) Assignee: Saied Jamshidi, Potomac, MD (US)

( * ) Notice: Subject to any disclaimer, the term of this patent is extended or adjusted under 35 U.S.C. 154(b) by 721 days.

(21) Appl. No.: 12/245,717

(22) Filed: Oct. 4, 2008

(65) Prior Publication Data
US 2010/0087825 A1     Apr. 8, 2010

(51) Int. Cl.
*A61B 17/70* (2006.01)
(52) U.S. Cl. ......................................... 606/249
(58) Field of Classification Search ........... 606/248–249
See application file for complete search history.

(56) References Cited

U.S. PATENT DOCUMENTS

| | | | |
|---|---|---|---|
| 5,772,661 A | 6/1998 | Michelson | |
| 2005/0240182 A1* | 10/2005 | Zucherman et al. | 606/61 |
| 2006/0259037 A1* | 11/2006 | Hartmann et al. | 606/61 |
| 2008/0183211 A1* | 7/2008 | Lamborne et al. | 606/249 |

* cited by examiner

*Primary Examiner* — Kevin T Truong
*Assistant Examiner* — Sameh Boles
(74) *Attorney, Agent, or Firm* — MaxvalueIP LLC

(57) ABSTRACT

A new Intra-spinal decompression implant is introduced that comprises of two plate attachments to a titanium metal implant that fits between the spinous processes of the vertebrae in the lower back, decompressing the neuro elements. The invention has a number of new design features including: double axis adjustable side plates, stepped conical tipped body and piercing tips on side plates, among many mentioned in this disclosure, that improves the quality of the surgery and the result for the patient. More examples are given in this application.

3 Claims, 11 Drawing Sheets

ADVANCED INTRA-SPINAL DECOMPRESSION IMPLANT

BACKGROUND OF THE INVENTION

An Intra-spinal decompression implant comprises of two plate attachments to a titanium metal implant that fits between the spinous processes of the vertebrae in the lower back, decompressing the neuro elements. These devices are implanted without fixation to the bone or ligament to preserve physiological spinal motion. These devices are particularly useful for patients who suffer from degenerative disc disease, spinal stenosis, or lateral recess syndrome. Such device has many advantages, including easy installation and therefore capable of decompressing the spinal canal and nerve roots quickly and efficiently.

The Intra-spinal decompression implants available to date in the market require different size of side plates and/or different size of implant body for different spinal levels or different patients. They are also prone to moving from the intended location.

This invention provides an improved design for Intra-spinal decompression implants that unlike other decompression implants on the market can be used on multiple spinal levels and different type of patients. The invented device will reduce surgery time by almost half an hour per spinal level and allows for the procedure to be done on local standby and on an out-patient basis.

SUMMARY OF THE INVENTION

One embodiment of the present invention is an Intra-spinal decompression implant that comprises of two plate attachments to a titanium metal implant that fits between the spinous processes of the vertebrae in the lower back, decompressing the neuro elements. The invention (as an example) has a number of new design features, including:

Lateral and vertical side plate adjustments
An implant body capable of dual axis adjustment with a large cavity for packing of bone graft material, for tissue to fuse around and inside the device, for better installation (the cavity can be multiple cavities, in middle, and small ones on the sides, as one example)
The implant body design incorporates a stepped and pointed conical tipped end, for better installation
Conical piercing tipped studs for attachment to the vertebrae
The implant design incorporates precision-machined slots and keys in the implant body and side plates

DETAILED DESCRIPTION OF THE PREFERRED EMBODIMENTS

Figure 1:
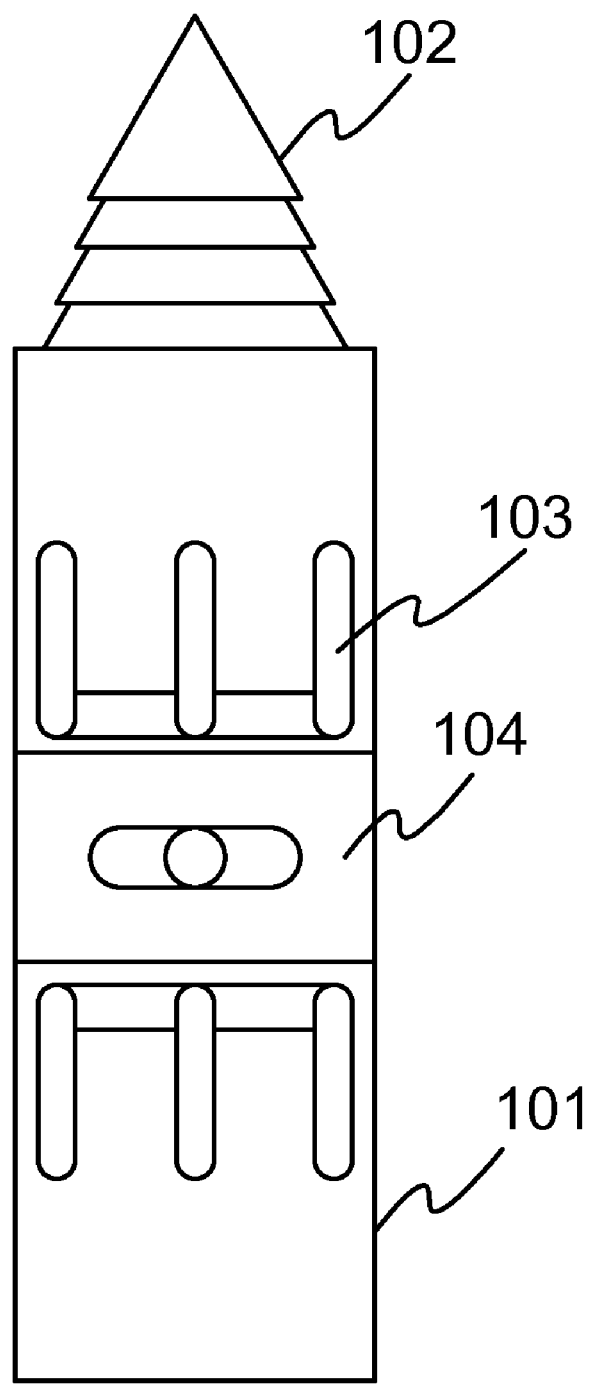
FIG. 1 is the top view of the implant body that incorporates a stepped and pointed conical tipped end.
Figure 2:
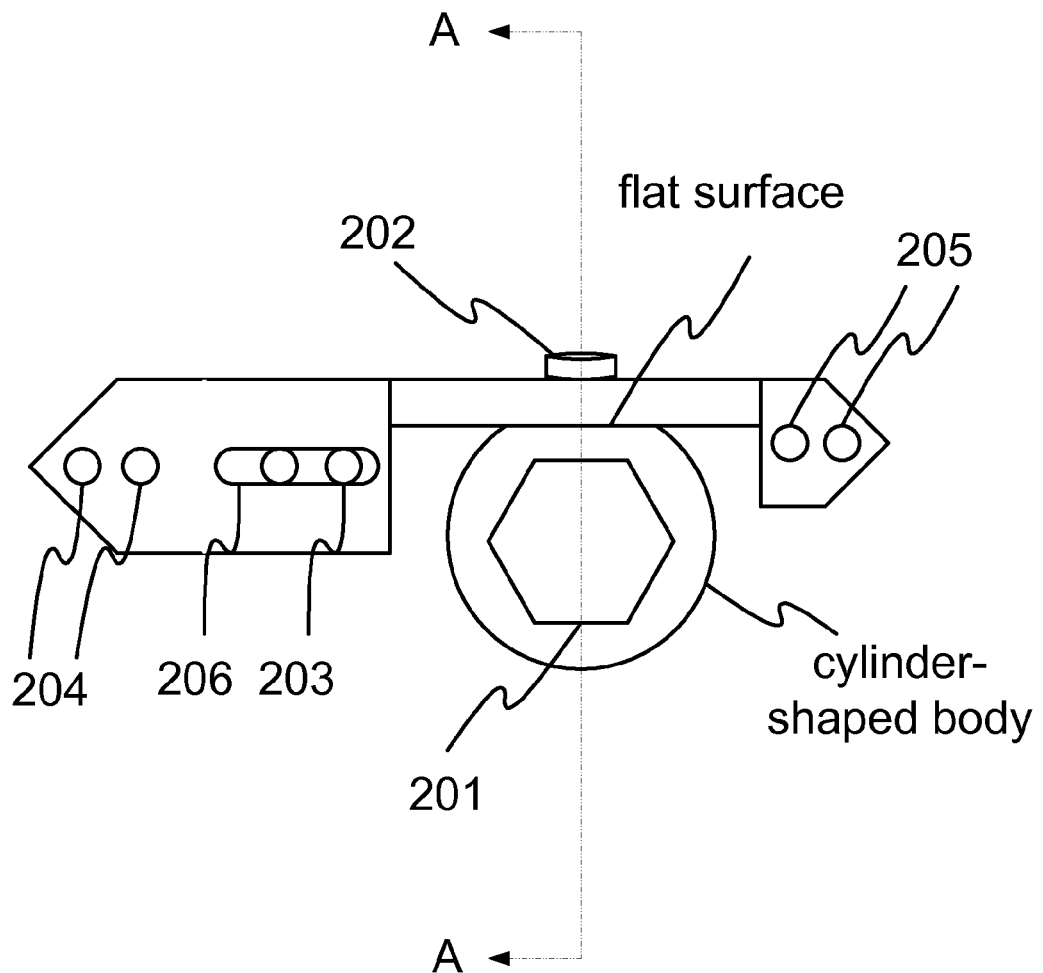
FIG. 2 illustrates one of the side plate attachments to the implant body, with rear and front parts, in which the length of the front part is adjustable.
Figure 3:
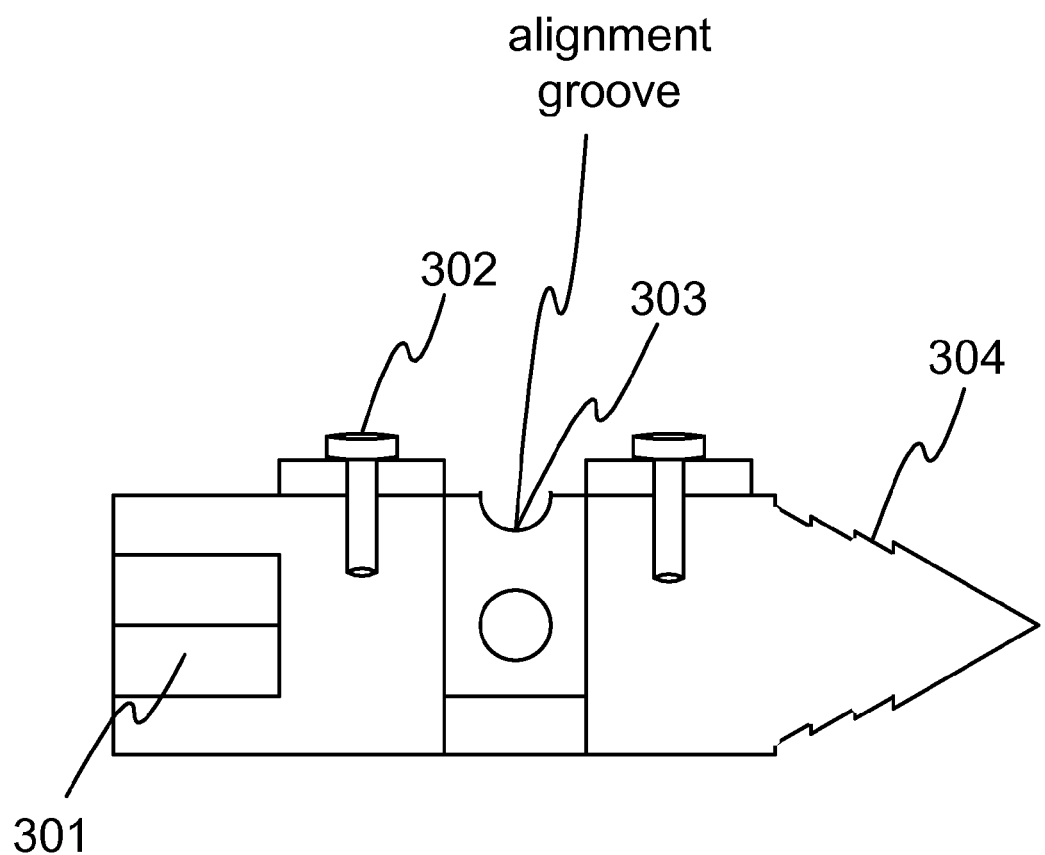
FIG. 3 is a cross section view of the implant body, which shows how the side plate is attached to the implant body as well as the bottom cavity of the implant body.
Figure 4:
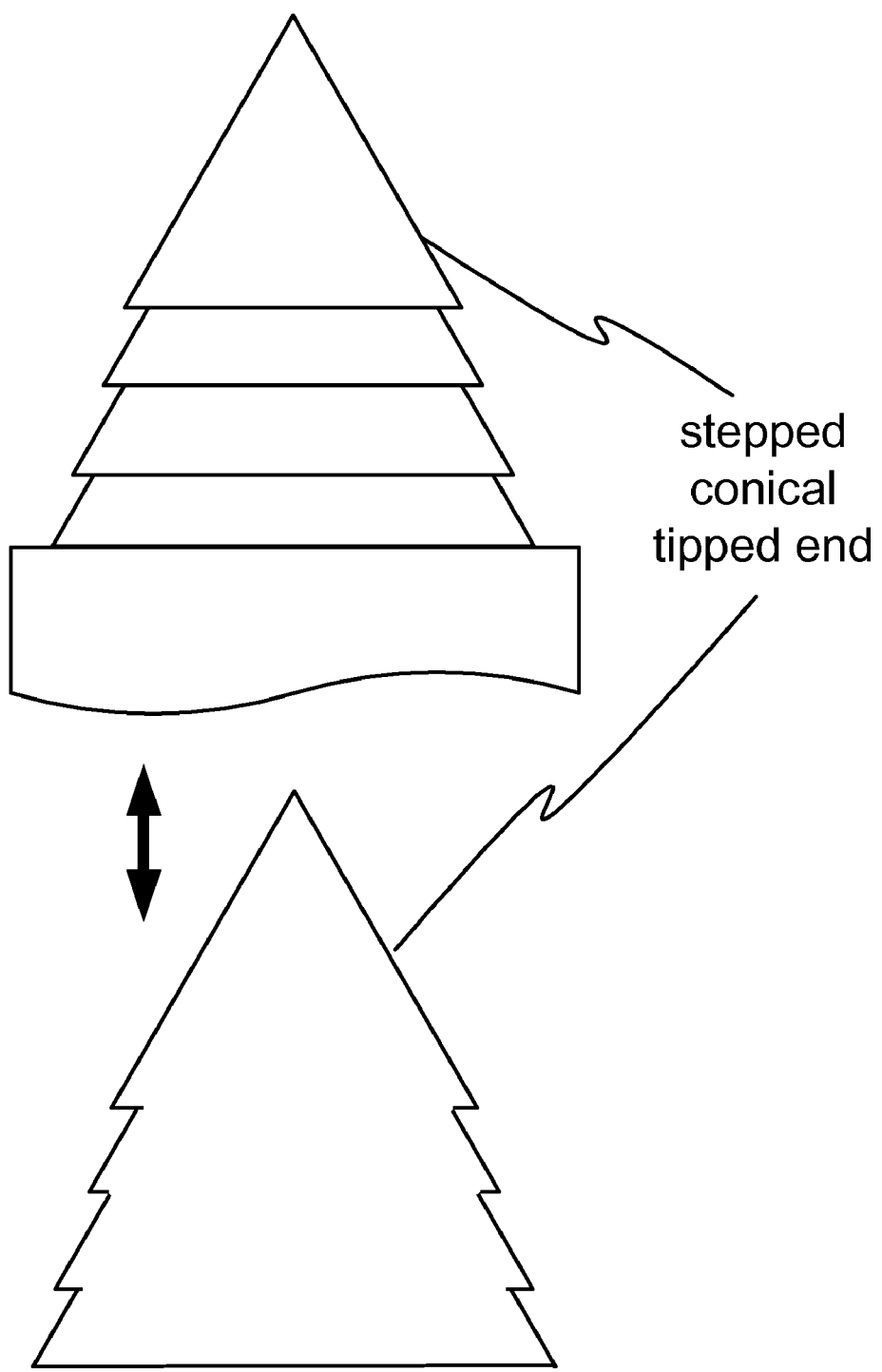
FIG. 4 shows the stepped and conical ripped end and its cross section.
Figure 5:
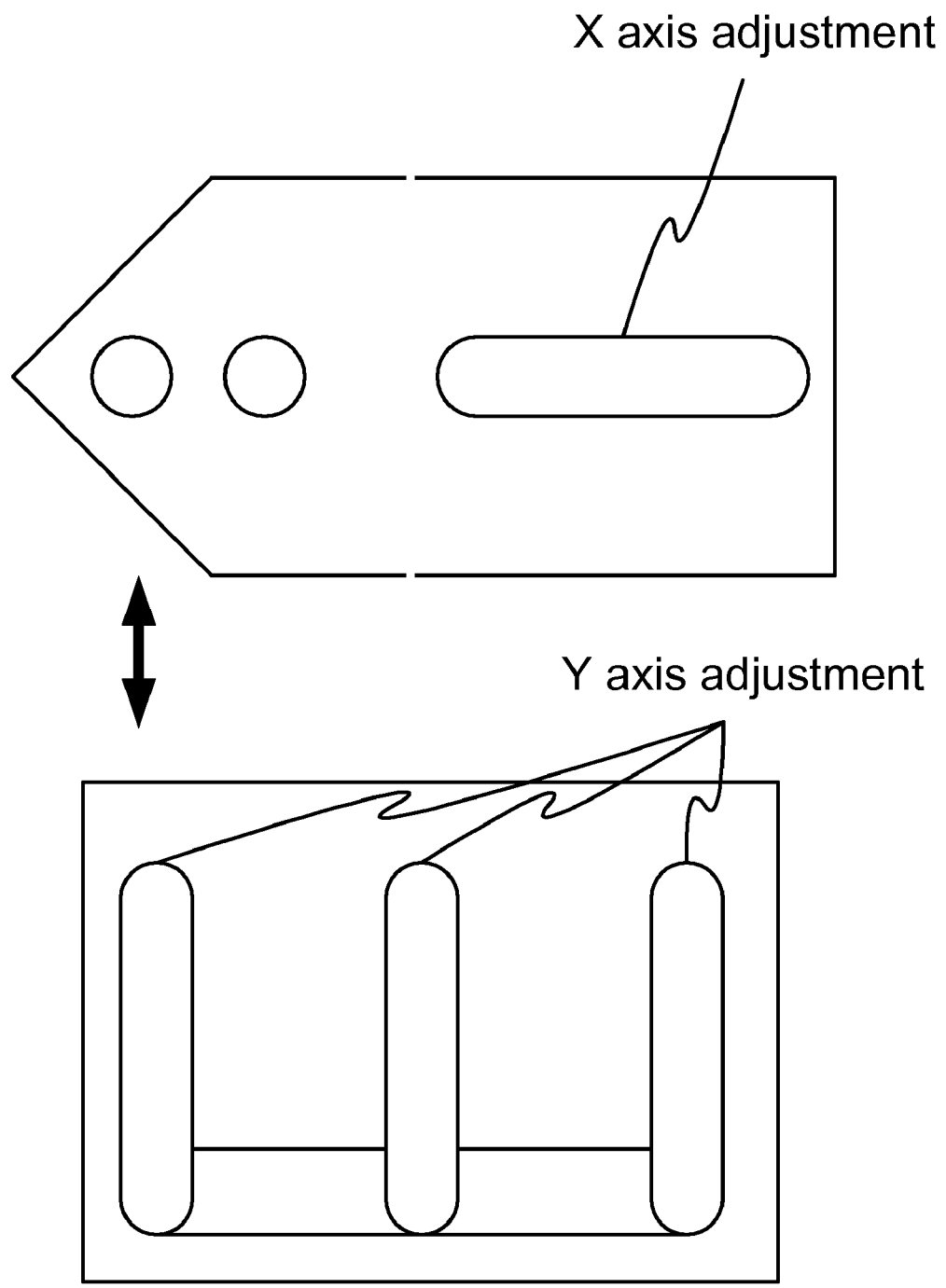
FIG. 5 shows the dual axis (X and Y) adjustment mechanisms of the implant.

The Intra-spinal decompression implant of the preferred embodiment is shown in FIGS. 1, 2 and 3. It is designed for plate attachment to the titanium metal implant and fits between the spinous processes of the vertebrae in the lower back, decompressing the neuro elements. It is designed to remain safely and permanently in place as the spinal processes gradually fuses together while the spine naturally repairs itself. The device is particularly useful for patients who suffer from degenerative disc disease, spinal stenosis, or lateral recess syndrome. The device has many advantages, including easy installation and therefore capable of decompressing the spinal canal and nerve roots quickly and inefficiently. Unlike other decompression implants on the market, the side plates of the device are adjustable in two dimensions (FIG. 5), which allow them to be universally used on multiple spinal levels or different patients. The device will reduce surgery time by almost half an hour per spinal level and allows for the procedure to be done on local standby and on an out-patient basis.

Figure 9:
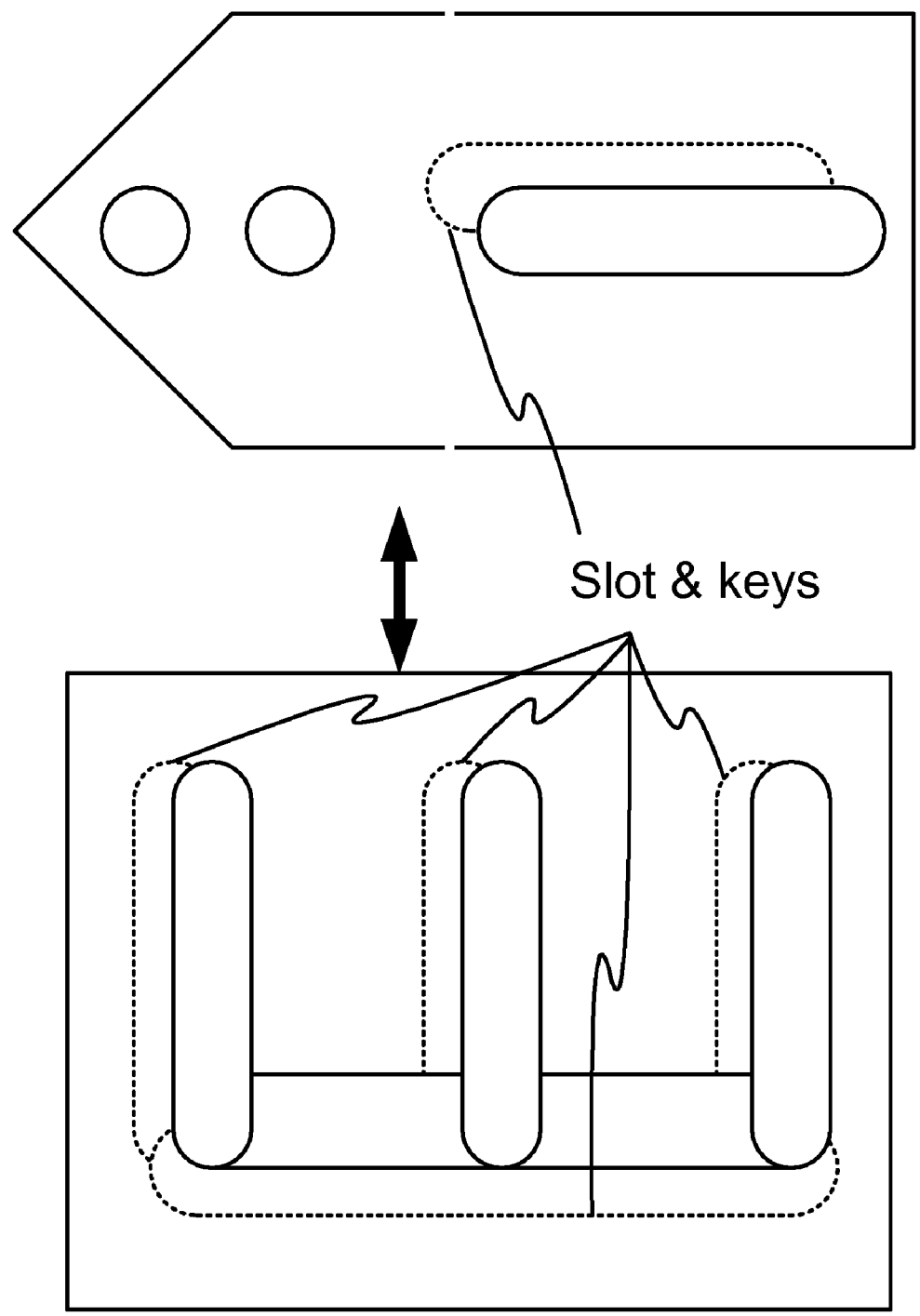
FIG. 9 shows the slot and key mechanism used for dual axis adjustment of the implement.
Figure 10:
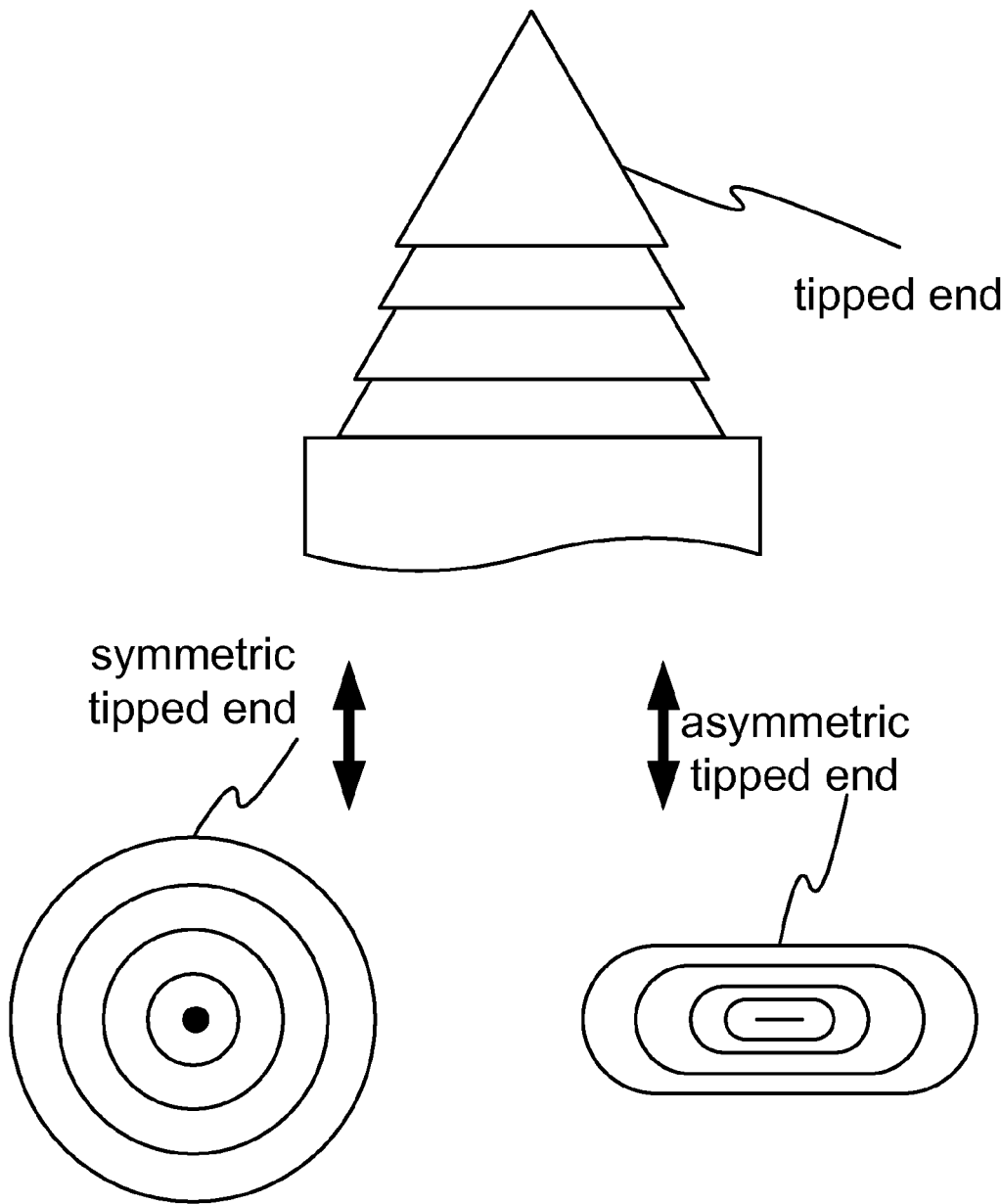
FIG. 10 shows a symmetric and an asymmetric stepped tipped end of the implant body.

The design includes implant adjustments in width and length to accommodate the patient anatomy. Height adjustment is accomplished by replacement of the implant body to a different diameter (larger or smaller size). The side plates are universal and can be assembled with a variety of sizes. Lateral and vertical adjustment (length and width) is accomplished by means of slots and keys (FIG. 9) that are machined in the side plate and implant body.

Design Features

Figure 6:
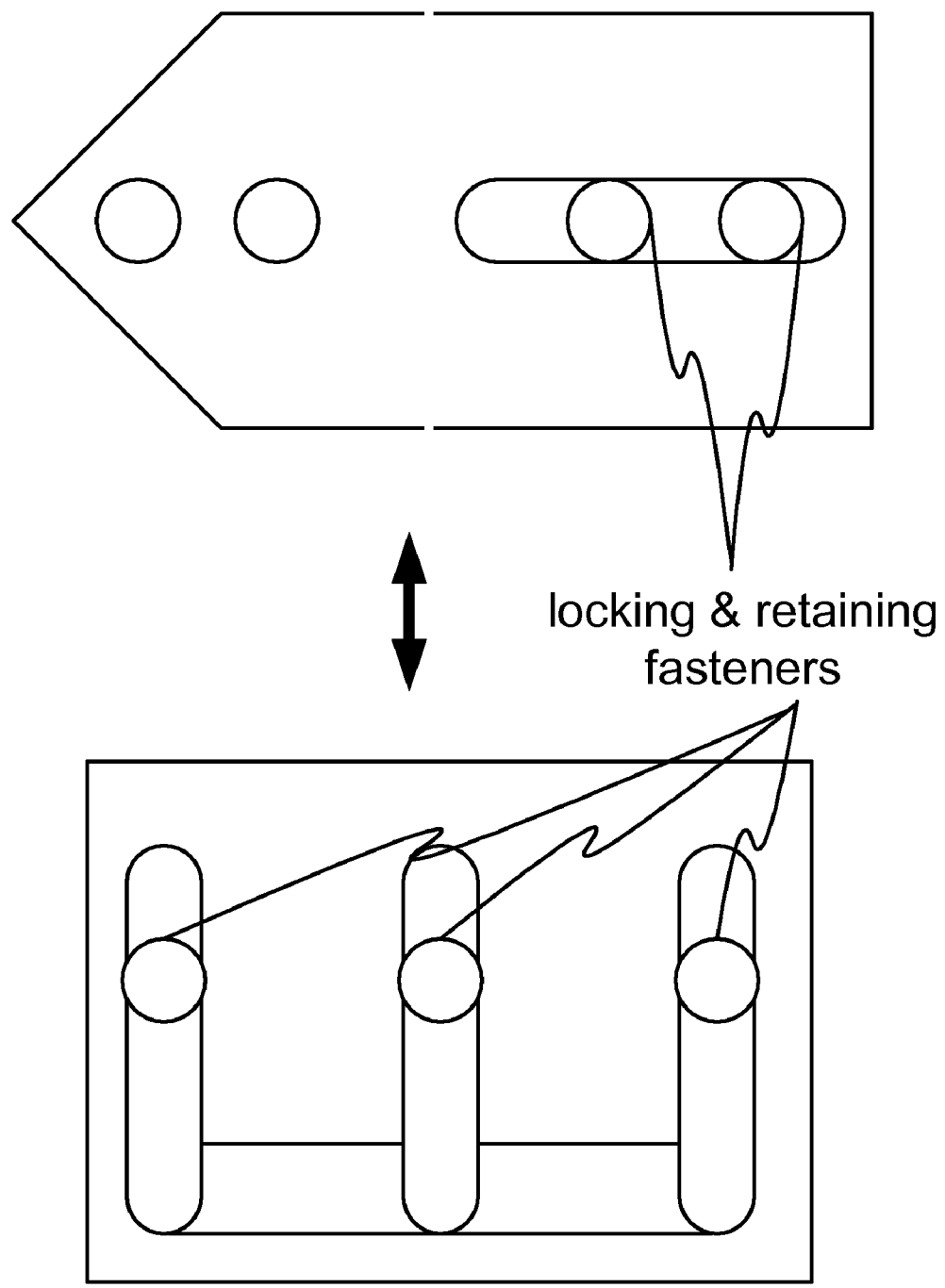
FIG. 6 shows the locking and retaining fasteners for the side plate attachment.

The design incorporates the following features for trouble-free implantation:

Lateral and vertical side plate adjustment incorporating ¼-½ turn locking and retaining fasteners (FIG. 6) that enables multiple positioning that accommodate a variable size range of patient anatomy. The side plates could be quickly adjusted before or during the surgery, therefore, reducing the operation time. FIG. 1 shows the slots (103) that are used for lateral adjustment of the side plates. There are typically 3 adjustment slots for each of the side plates as shown in FIG. 1 (103). FIG. 2 shows one of the side plates, which has vertical adjustment via a slot (206) and typically two screws (203).

Figure 7:
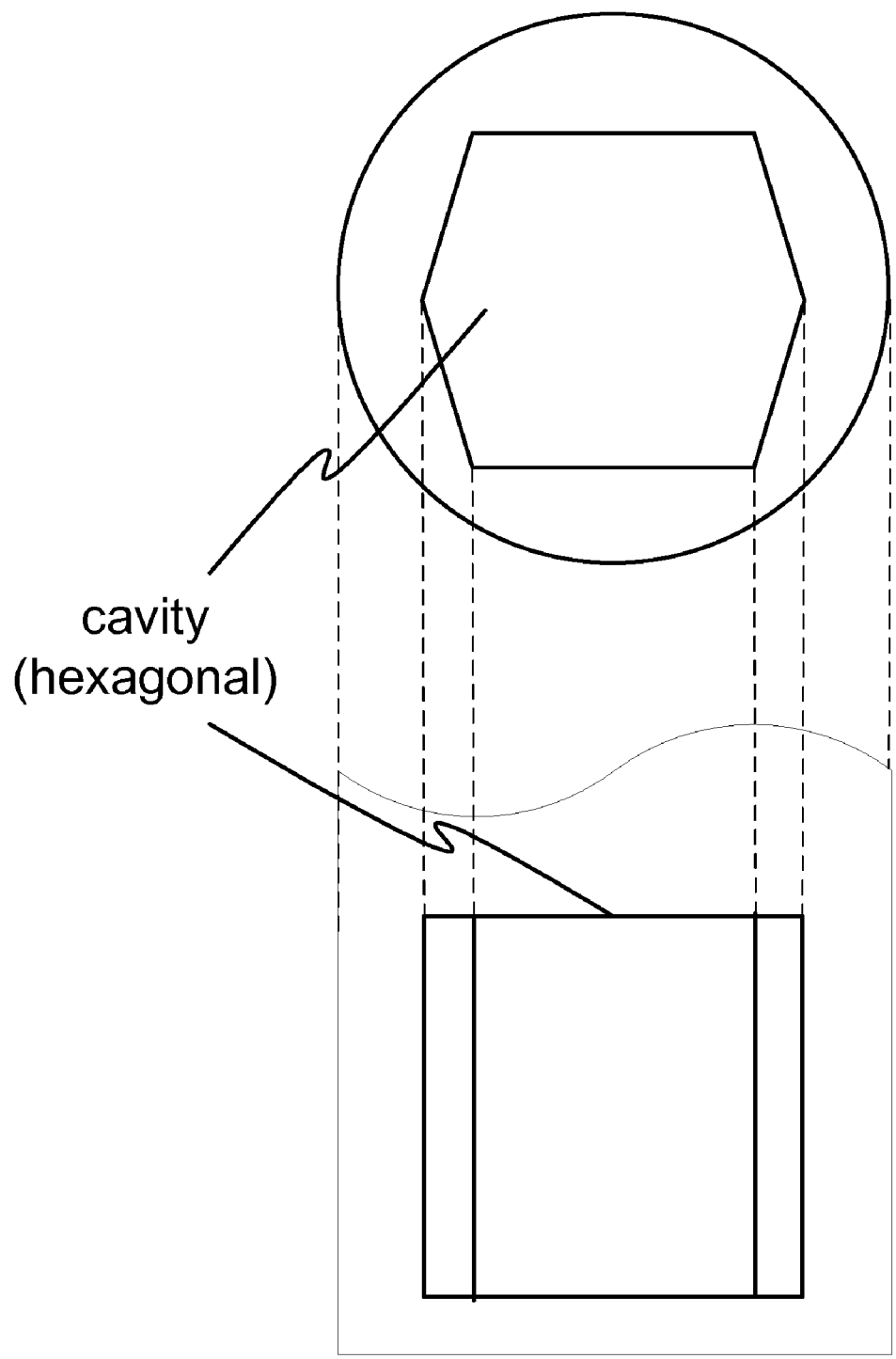
FIG. 7 shows the large bottom cavity of the implant body. This example shows a hexagonal shaped cavity.

An implant body that is capable of dual axis adjustment with a large cavity (FIG. 7) for multiple purposes, which include engaging the insertion handle, packing of bone graft material, and reducing the weight of the implant as shown in FIG. 3. The cavity has preferably a octagon or hexagon shape (301). The implant body may come in different diameter and lengths to accommodate different patient compositions. It could also be made of different materials that may include non-corrosive metals such as Titanium, plastic natural or man-made material.

The implant body design incorporates a stepped and pointed conical tipped end as shown in FIGS. 1 and 3 that promotes easier insertion into the patient (between the spinoud processes of the vertebrae in the lower back) and prevents excessive movement of the implant after surgery. The tipped end (102, 304) may be asymmetric for easier insertion.

Figure 8:
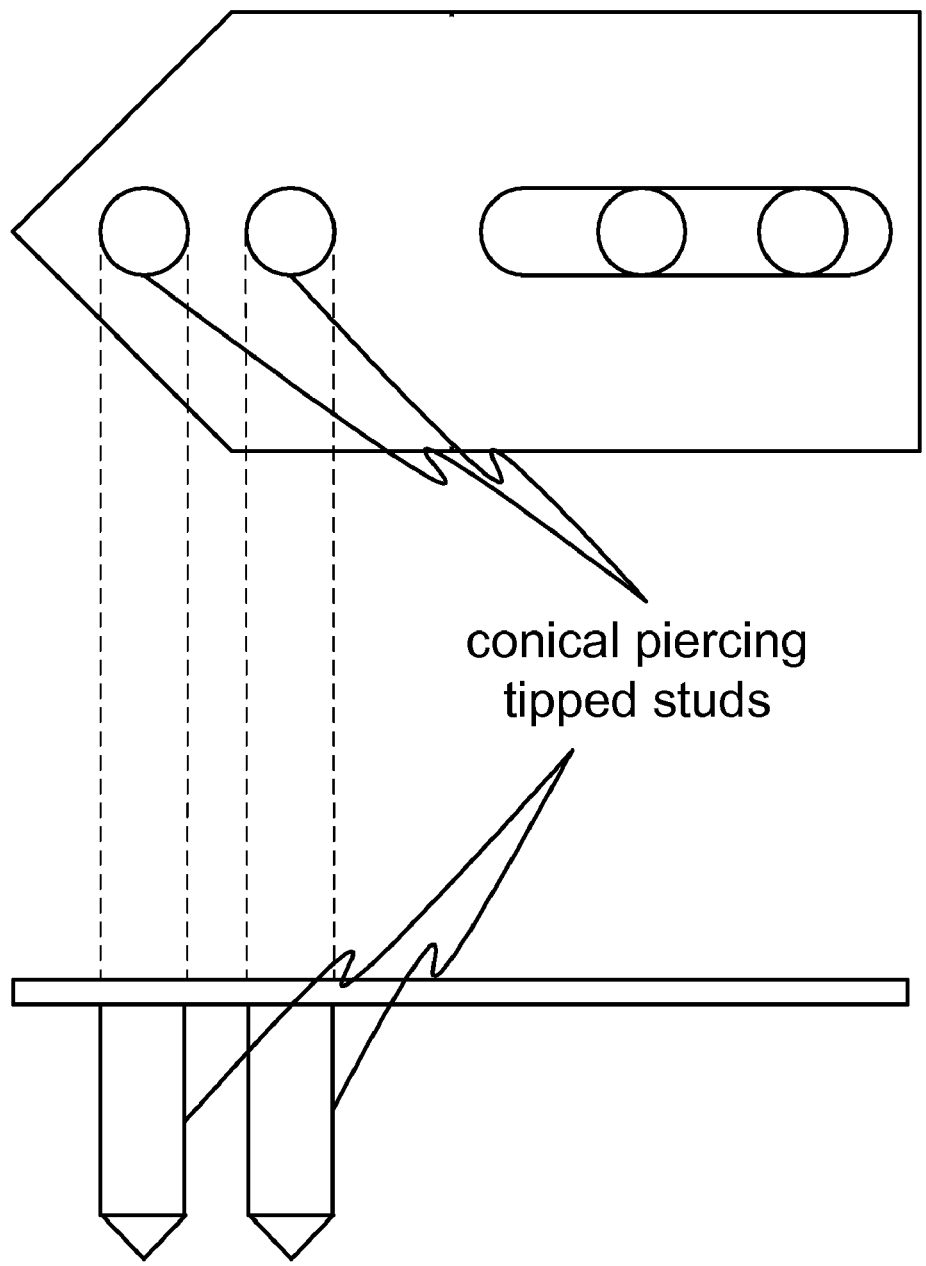
FIG. 8 shows the conical-shaped piercing tipped studs on the front and rear side plates

Conical piercing tipped studs (FIG. 8) on side plates for attachment to the vertebrae and therefore reducing the chance of the implant moving from its preferred spot shown in FIG. 2 (204, 205). Preferably two tipped studs are placed in the front (204) and two on the rear (205) of each side plate.

The implant design incorporates precision-machined slots and keys (103, 302, and 303) in the implant body and side plates to obtain a smooth running and sliding fit that prevent binding and allow for quick and easy adjustments in both lateral and vertical directions to accommodate a variety of patient compositions. The precision-machined slots allow for speedy and symmetrical installation of side plates, and therefore, reducing the operation time.

In one embodiment, the shape of the implant in 2 directions have 2 different cross-sections, one much larger, being asymmetric, making it ideal for locking and proper installation, for example, after rotation of the assembly by 90 degree, making sure that the device cannot be slide out (out of its intended position), for example, being locked at that direction, for proper and long-lasting installation in the body.

In one embodiment, the plates can be adjusted for multiple levels for vertebral body.

In another embodiment, the size is adjustable for different size patients, making it cheaper to manufacture, and easier to install, because it does not have to be custom-made much before the surgery, for each individual separately, based on his/her size and body structure.

Figure 11:
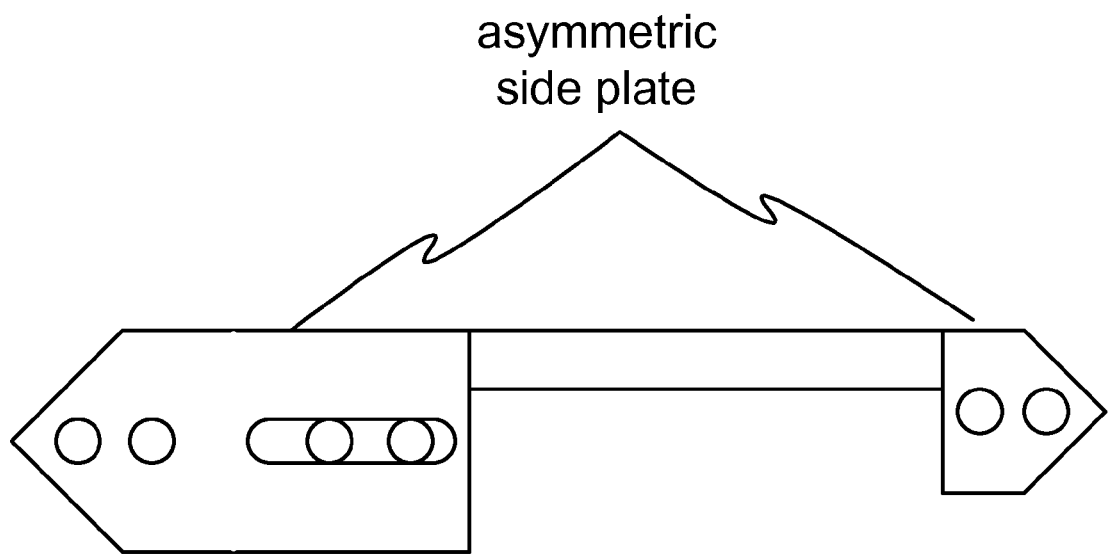
FIG. 11 shows an asymmetric side plate, with different front and rear wings sizes.

In one embodiment, the side plates are asymmetrical and the front and rear end of the side plates have different size (FIG. 11).

Note that easy installation means faster surgery, which means better survival rate after surgery.

The attachments with screws, holes, slots, and pins make the size adjustable for different patients and sizes.

Any material, such as plastic, titanium, alloy, metal, elastic, human tissue, animal tissue, cultured material, plant-based, oil-based, petrochemical, cotton, fabric, any byproducts, magnetic, non-magnetic, alloyed, plated, implanted, mix, powder, combination, mixture, and similar types, can be used.

The attachments can be done by screws, holes, slots, pins, ribbon, string, chain, cable, rings, human tissue, engineered tissue, glue, pressured material, Velcro-type, micro-sized devices, nano-fabricated material and devices, using only surface adhesion, using micro-property of materials, welded joints, hinges, locks, engagements devices, keys, and similar types.

Any variations of the above are also meant to be covered by the current patent application.

The invention claimed is:

1. An apparatus for decompressing spinal neuro elements, said apparatus comprising: an implant body, wherein said implant body has an asymmetric cross section; said implant body comprises two parallel flat sides and two curved sides, wherein minimum distance between said two parallel flat sides is smaller than minimum distance between said two curved sides; said implant body comprises a base with a hexagonal cavity; said implant body comprises a tip with a stepped and pointed conical shape; and said implant body comprises one or more grooves on said flat sides for passage of ligament;

two side plates, wherein said two side plates are positioned in parallel on one of the flat sides of said implant body, wherein minimum distance between said two side plates is adjustable, wherein each of said two side plates comprises one or more slots for adjusting position of said two side plates with respect to said implant body; length of each of said side plates is adjustable; each of said two side plates comprises one or more conical piercing tipped studs for attachment to human body or tissue;

and locking and retaining fasteners, wherein said two side plates are attached to said implant body using said locking and retaining fasteners, wherein said implant body comprises holes for receiving said locking and retaining fasteners.

2. An apparatus as stated in claim 1, wherein said implant body and said two side plates are made from metal, alloy, plastic, elastic, natural, titanium or man-made material.

3. An apparatus as stated in claim 1, wherein said apparatus has a rough surface or small extensions for better friction, adhesion, and incorporation to said human body or tissue.

\* \* \* \* \*